United States Patent [19]

Wdowik

[11] Patent Number: 5,587,156
[45] Date of Patent: Dec. 24, 1996

[54] SHAVING COMPOSITIONS CONTAINING PARTICULATE ADDITIVES

[75] Inventor: Mark S. Wdowik, Ft. Collins, Colo.

[73] Assignee: Critical Dimension, Incorporated, Ft. Collins, Colo.

[21] Appl. No.: 634,602

[22] Filed: Apr. 18, 1996

[51] Int. Cl.$^6$ .............................. A61K 7/09; A01N 37/00
[52] U.S. Cl. .................... 424/73; 510/119; 510/158; 424/45; 424/47; 424/49; 424/50; 424/51; 424/52; 424/53; 424/54; 424/55; 424/56; 424/57; 424/58; 424/59; 514/557; 514/772; 514/783; 514/944
[58] Field of Search ................ 252/95, 99, 102, 252/160, 120, 128, 130, 131, 155, 174.21, 174.23, 542, 548; 424/45, 47, 49–58; 514/557, 772, 63, 558, 783, 944

[56] References Cited

U.S. PATENT DOCUMENTS

| | | | |
|---|---|---|---|
| 3,541,581 | 11/1970 | Monson | 53/104 |
| 3,852,417 | 12/1974 | McLaughlin | 424/47 |
| 4,051,056 | 9/1977 | Hartman | 252/99 |
| 4,145,411 | 3/1979 | Mende | 424/45 |
| 4,155,870 | 5/1979 | Jorgensen | 252/131 |
| 4,157,387 | 6/1979 | Benedict | 424/54 |
| 4,187,288 | 2/1980 | Cordon et al. | 424/49 |
| 4,735,746 | 4/1988 | Speranza et al. | 252/544 |
| 4,786,432 | 11/1988 | Kanfer et al. | 252/120 |
| 4,917,884 | 4/1990 | Roberts | 424/73 |
| 4,994,265 | 2/1991 | White | 424/73 |
| 4,999,183 | 3/1991 | Mackles et al. | 424/47 |
| 5,034,220 | 7/1991 | Helioff et al. | 424/73 |
| 5,174,992 | 12/1992 | Lindauer et al. | 424/73 |
| 5,298,181 | 3/1994 | Choy et al. | 252/95 |
| 5,326,556 | 7/1994 | Barnet et al. | 424/73 |

*Primary Examiner*—Terressa Mosley
*Attorney, Agent, or Firm*—Donald W. Margolis

[57] ABSTRACT

Shaving compositions for use in the personal shaving process with a razor blade assembly include insoluble solid particulate additives. The shaving compositions include a mixture of at least one wetting agent, at least one cleansing agent, at least one lather producing composition, and at least one emollient; and further include at least one solid, insoluble particulate additive in a well dispersed suspension throughout said shaving composition. The solid additives are present in an effective amount to produce physical microscopic support for the blade of a razor blade assembly during the personal shaving process. By providing microsupport of the razor blade parallel to skin surface and above surface irregularities, the solid particulate additives provide improved razor blade glide, thereby preventing nicks and cuts, and also enhancing exfoliation of dead skin and removal of grease and oils, as well as improving hair extraction prior to cutting, thereby improving overall smoothness of the post-shaven skin. The shaving compositions may be in the form of a gel, cream, solid, liquid or aerosol.

21 Claims, No Drawings

SHAVING COMPOSITIONS CONTAINING PARTICULATE ADDITIVES

I. BACKGROUND OF THE INVENTION a. Field of the Invention

The present invention relates to shaving compositions which include particulate additives, and more particularly to shaving compositions, whether in the form of a solid, gel, cream, liquid, or aerosol which include solid, insoluble particulate additives.

b. Description of the Related Art

Solid particulate additives have been employed in a host of cleansing compositions for use in the removal of foreign materials, as well as dead skin cells from the skin surface. These well known cleansing compositions are described, for example, in U.S. Pat. No. 4,155,870, in which glass bubbles are incorporated into the cleansing medium, and U.S. Pat. No. 4,157,387 which describes a cleansing composition incorporating a water soluble polymer as an abrasive for use in cleaning the skin and for removing dead skin cells from the skin surface. The art of incorporation of fillers and abrasive additives in soaps is well known and described in prior art such as Kanfer, et. al., in U.S. Pat. No. 4,786,432. Other examples of soap compositions containing particulate additives are disclosed in U.S. Pat. Nos. 4,187,288 by Cordon, et. al., 4,735,746 by Speranza, et. al, 4,051,056 by Hartman. In each of these references abrasive impregnated soap provide excellent scrubbing action, thereby producing not only a cleaning action, but also superior post-cleansing skin smoothness.

Conventional shaving compositions, whether in solid, gel, cream, liquid or aerosol form, generally include complex lather producing chemical compositions or foam inducing agents. Typical shaving compositions are described in U.S. Pat. Nos. 3,852,417 by McLaughlin, 4,145,411 by Mende, 5,034,220 by Helioff, et. al., 4,999,183 by Mackles, et. al., and 5,326,556 by Barnet, et al. These shaving compositions all contain wetting agents or surfactants, and foaming agents. These prior art shaving compositions typically contain five to fifteen percent by weight stearate soap, such as sodium stearate, potassium stearate, or mixtures thereof with weight ratios in the range of about 2:1 to about 8:1. They also include emollient additives such as coconut fatty acids, castor oil, coconut oil, or other complex oils. Lubrication is achieved in shaving compositions by employing a combination of one or more of the aforementioned oils and fatty acid monoethanolamide or diethanolamide. Such shaving compositions also include wetting agents or surfactants to enhance adherence of the media to the to-be-shaved hair and surrounding skin. Furthermore, wetting agents also provide some degree of and limited physical support for the shaving blade, thereby improving blade glide and reducing skin irritation. Furthermore, the compositions described in prior art include claims for additives such as inorganic salts which enhance lubrication; however, these additives, such as those described in U.S. Pat. No. 3,852,417 by McLaughlin, are water soluble additives such as polysiloxanes in amounts of up to 5 percent by weight, or water soluble polymeric materials of up to 5 percent by weight, such as polyvinylpyrrolidone or polyethylene oxide.

It is therefore seen that current shaving compositions, whether provided in the form of a solid, gel, cream, liquid or aerosol, include materials which provide three basic characteristics which are associated with hair removal by the process of shaving with a razor blade assembly:

(a) Wetting: using surface acting agents, otherwise known as wetting agents or surfactants, which allow the shaving composition to better adhere to the surface of the skin and hair, thereby producing improved softening of the hair, removal of grease and oils from the skin and hair, and improved removal of the shaving composition during the rinsing phase, after shaving is completed;

(b) Lathering and lubrication: with gelling aids and post-foaming agents, such as described in U.S. Pat. No. 3,541,581 by Monson, are employed to create a thin boundary layer between the shaving blade and the skin, thereby serving to cushion the shaving blade from the skin in order to prevent nicks and cuts, and also serving to reduce skin irritation, as well as to support the hairs to cause them to assume an erect position, thereby setting the hair up for the shaving razor blade assembly to provide improved hair removal; and (c) Softening: with emollients and skin conditioners are incorporated in shaving media to open skin pores, soften the hairs, and soften the exposed skin. Typical emollients are described in U.S. Pat. Nos. 4,994,265 or 4,917,884.

In the same manner, it is well known in the prior art that many cleansing soaps include cleansing agents in order to remove foreign materials and dead skin from the surface of the skin, including hands, face, and legs. Such cleansing agents have been reported in prior art U.S. Pat. Nos. 4,155,870; 5,298,181; and 4,051,056. These cleansing agents produce added scrubbing action in conjunction with a soap to provide effective removal of stubborn stains, foreign materials, irregular skin surfaces, and dead skin cells, leaving the post-cleansed skin surface ultra-smooth. For example, facial cleanser scrubs have been in use for many years to smooth rough features and remove grease, oils, and dead skin cells. However, this application has never been applied toward shaving compositions, whether applied to the face, or the legs or underarms.

A U.S. safety razor manufacturer, recently introduced a new type of woman's razor blade assembly called the Schick Safe Effects™, whereby the blade or assembly of multiple blades is enclosed in a fine wire wrapping. The support wire provides blade support above the skin surface to provide a nick free shave. However, due to relatively large diameter of the support wire employed, the shaving blade does not produce as close a shave as a razor blade assembly that does not include a wire.

It is therefore seen that there still remains a need for a shaving medium composition which provides a nick free shave, yet which provides a close shave such as one would get with a standard razor blade assembly. It is further seen that no prior art shaving compositions are known which include solid, totally insoluble particles as a part of their formulation. As a matter of fact, the thought of including solid, insoluble particles in shaving compositions might appear to be offensive and counter-intuitive for a material which is applied to the face.

SUMMARY OF THE INVENTION

It is therefore an object of the present invention to provide shaving compositions for use with conventional razor blade assemblies which minimize nicks and cuts, and which yet provide close shaves.

It is another object of the present invention to provide a shaving composition in which insoluble particulate additives, such as filler or abrasive materials, are incorporated to reduce undesired nicks and cuts, and improve post-shave skin smoothness.

It is another object of the present invention to provide an improved shaving composition with improved cleansing characteristics.

It is a further object of the present invention to provide an improved shaving composition which reduces nicks and cuts, and which improves post-shave smoothness regardless of the form of the shaving composition, that is solid, gel, cream, liquid or aerosol.

These and other objects of the invention are achieved by the shaving compositions of the present invention which include an effective amount of insoluble particulate additives, such as inorganic or organic solids or fillers, which additives provide physical, microscopic blade support.

As used herein the term "razor blade assembly" means either a straight razor or a safety razor with one or more shaving edge. As used herein the term "shaving compositions" means compositions utilized specifically as a lubricant and blade support for the shaving process, and which include wetting agents, surfactants, foaming agents or lather producing compositions, gelling aids and post-foaming agents, emollients, cleansing agents, and equivalents thereof, and regardless of the form of the shaving composition, that is solid, gel, cream, liquid or aerosol. As used herein the term "particulate additives" means insoluble inorganic or organic solids or filler particles, and equivalents thereof, having a size in the range of from about 0.1 μm to about 1,000 μm, with particles in the range of about 10 μm to 500 μm being practical, and 50 μm to 200 μm being preferred, although other sizes may be utilized, as discussed below. A single particulate additive or combinations of particulate additives may be used in the shaving compositions of the present invention. As used herein "an effective amount" of insoluble particulate additives is an amount, by weight, which provides physical support for the blade of a razor blade assembly during the personal shaving process. In most instances, from about 0.1% to about 20%, by weight will be adequate, while from about 1% to about 10%, by weight is normally preferred. However, it is to be understood that in some instance an equivalent "effective amount" of insoluble particulate additives less than 0.1% and/or greater than 20%, by weight, and in thick pastes and gels even as high as 90% or greater may be used in the practice of the present invention. When used in shaving compositions the strictly insoluble particulate solid additives are present as a well dispersed suspension throughout the composition. Insoluble particulate additives which have particular utility in the practice of the present invention include abrasives, and organic solids such as polymeric beads or cylindrical shaped polymeric particles, or synthetic organic fibers, such as the cleansers described in Speranza, et al. U.S. Pat. No. 4,735,746.

The use of such particulate additives in the shaving compositions of the present invention provide microscopic support for the razor blade assembly during shaving, thereby providing a close but nick free shave with a standard razor blade assembly. In addition to providing microscopic support for the blade, these solid particulate additives also work in conjunction with the razor blade assembly and the user's scrubbing movements during shaving composition application to remove dirt, oils, stains, and dead skin cells from the skin's surface, thereby producing post-shave skin surfaces with improved smoothness and cleanliness as compared to those provided by current, commercially available shaving compositions. Furthermore, the particulate additive solid particles in the shaving compositions of the present invention improve the hair extraction process performed by the shaving blade assembly prior to the blade cutting the hair by: (1) depressing the surface of the skin during shaving so that the post-shave position of the cut hair resides below the surface of the skin, and (2) extracting the hair away from its follicle just prior to being cut, thereby improving the overall smoothness of the post-process skin.

These and other objects of the present invention will become apparent to those skilled in the art from the following detailed description, showing the contemplated novel compositions as herein described, and more particularly defined by the appended claims, it being understood that changes in the precise embodiments to the herein disclosed invention are meant to be included as coming within the scope of the claims, except insofar as they may be precluded by the prior art.

DETAILED DESCRIPTION OF THE INVENTION

The present invention provides new and improved shaving compositions which include insoluble particulate additives. The particulate additives incorporated into the shaving compositions of the present invention serve multiple purposes and provide several benefits. First, the particulate additives provide microscopic support to the razor blade assembly and superior blade glide by providing physical, parallel support of the blade edge as it moves over the skin surface, and especially over skin irregularities. This microglide support system promotes nick-free shaves, with ultra-smooth post-shave skin smoothness. Second, the solid particles act in conjunction with the blade assembly to extract each hair away from its follicle, just prior to being cut. As a result the post-shave position of each cut hair resides below the surface of the skin, thereby improving the overall smoothness of the post-process skin. Third, the particulate additives cooperate with the cleansing agents in the shaving compositions to produce added scrubbing action in conjunction with a soap constituent to provide effective removal of dirt, oils, stains, and dead skin cells, foreign materials, irregular skin surfaces, and dead skin cells, thereby leaving the post-cleansed skin surface extremely smooth.

The present invention is not limited to any single shaving composition, but rather to the concept of the inclusion of suitable particulate additives to any shaving composition, regardless of its form before or after it is applied, that is solid, gel, cream, liquid or aerosol.

EXAMPLE 1

One preferred exemplary shaving composition of the present invention is based on that described in U.S. Pat. No. 3,852,417 by McLaughlin, but includes added water insoluble organic additives is as follows:

| Material | % by Weight |
|---|---|
| Potassium stearate | 5.20 |
| Sodium stearate | 1.11 |
| Lauric acid diethanolamide | 1.60 |
| Mineral oil (Saybolt viscosity of 75–100 seconds at 100° F.) | 15.00 |
| Stearic Acid | 0.14 |
| Coconut fatty acid | 0.68 |
| Glycerine | 3.20 |
| Polyvinylpyrrolidone (Grade K-30) | 0.12 |
| Perfume | 0.37 |
| Water | 57.58 |
| Dichlorodifluoromethane | 10.00 |
| Particulate additive - Nylon fibers | 5.00 |
| Total | 100.00% |

The nylon fibers in this example are preferably cylindrical particles nominally about 50 μm in diameter and a nominal length of about 200 μm, although other sizes may be utilized as discussed below. The shaving composition in this example will be prepared by mixing 6.12 parts of stearic acid, 1.60 parts of lauric acid diethanolamide, 15 parts mineral oil and 0.68 parts of coconut fatty acids at a temperature in the range of about 167°–176° F., followed with agitation and admixture of 0.12 parts polyvinylpyrrolidone, 3.2 parts of glycerine, 0.9 parts of potassium hydroxide, and 0.2 parts of sodium hydroxide in 57.58 parts of water at a constant temperature in the range of about 167°–176° F. The resulting mixture will then be cooled to a temperature in the range of about 115°–125° F. with agitation. The perfume and particulate additive nylon fibers will then be added to the mixture, and the temperature cooled to the range of about between about 84°–88° F. This final liquid mixture will then be placed in an appropriate dispenser under pressure with the addition of propellant for use as an aerosol cream.

When dispensed and applied to the face and used for shaving, this composition will provide a shaving experience in which the particulate additives in the shaving composition will provide microscopic support to the razor blade assembly and superior blade glide by providing physical, parallel support of the blade edge as it moves over the skin surface, and especially over skin irregularities, thereby will promote nick-free shaves, with ultra-smooth post-shave skin smoothness. The post-shave position of each cut hair will be found to reside below the surface of the skin, thereby improving the overall smoothness of the post-process skin. In addition, the particulate additives will cooperate with the cleansing agents in the shaving compositions to produce added scrubbing action to provide effective removal of dirt, oils, stains, and dead skin cells, foreign materials, irregular skin surfaces, and dead skin cells, and will thereby leave the post-cleansed skin surface extremely smooth.

When the formulation of EXAMPLE 1 is modified, first using 10% and then using 20%, by weight, insoluble nylon fibers, while in each instance proportionally decreasing amounts of water and/or Mineral oil, the resulting shaving compositions will provide a shaving experience which is equivalent to the original formula, suggesting that even greater amounts of insoluble particles can be used in the practice of the present invention.

EXAMPLE 2

Another exemplary composition is based on that described in McLaughlin U.S. Pat. No. 3,852,417, and includes the addition of abrasive inorganic additives, as follows:

| Material | % by Weight |
| --- | --- |
| Potassium stearate | 5.20 |
| Sodium stearate | 1.11 |
| Lauric acid diethanolamide | 1.60 |
| Mineral oil (Saybolt viscosity of 75–100 seconds at 100° F.) | 17.00 |
| Stearic Acid | 0.14 |
| Coconut fatty acid | 0.68 |
| Glycerine | 3.20 |
| Polyvinylpyrrolidone (Grade K-30) | 0.12 |
| Perfume | 0.37 |
| Water | 57.58 |
| Dichlorodifluoromethane | 10.00 |
| Particulate additive - silica sand | 3.00 |
| Total | 100.00% |

The silica sand employed in this example is nominally about 75 μm in size, although other sizes may be utilized as discussed below.

This shaving composition will be prepared by mixing 6.12 parts of stearic acid, 1.60 parts of lauric acid diethanolamide, 17 parts mineral oil and 0.68 parts of coconut fatty acids at a temperature in the range of about 167°–176° F., followed with agitation and admixture of 0.12 parts polyvinylpyrrolidone, 3.2 parts of glycerine, 0.9 parts of potassium hydroxide, and 0.2 parts of sodium hydroxide in 57.58 parts of water at a constant temperature in the range of about 167°–176° F. The subsequent mixture will then be cooled to a temperature of 115°–125° F. with agitation. The perfume and silica sand will be added to the mixture, and the temperature cooled to the range of about between about 84° to 88° F. This final liquid mixture will then be placed in an appropriate dispenser under pressure with the addition of propellant for use as an aerosol cream.

When the aerosol medium will be disbursed from its container onto the skin surface, either directly or upon admixture of the medium in a suitable container or in the hand of a user, it will quickly foam, and when applied to the face it will wet the surface of the skin, softening the skin surface and the hair to be shaved, forcing the hair strands to stand erect normal to the surface of the skin, and opening skin pores. When a standard blade assembly will be subsequently employed over the surface of the skin, it will cut each strand of hair in its path, using the shaving medium as lubricant with each swath. Post-shave skin surfaces will be nick free and ultra-smooth.

Insoluble particulate additives which are suitable for incorporation into standard shaving media compositions in accordance with the present invention include, but are not limited to thermoplastic and thermosetting resin polymers and inorganic materials such as the following:

| | |
| --- | --- |
| a) polyamides (e.g. nylon) | b) polytetrafluoroethylene (Teflon) |
| c) acetal resins (Delrin) | d) polypropylene |
| e) polyethelenes | f) polyurethane |
| g) silica | h) pumice |
| i) wood dust | j) quartz |
| k) titanium dioxide | l) calcium carbonate |
| m) calcium phosphate | n) calcium silicate |
| o) aluminum oxide | p) silicon nitride |
| q) boron carbide | r) silicon carbide |
| s) diatomaceous earth | |

Because of the ability to shape synthetic fibers such as nylon or acetal resin, these materials are two of the preferred additive materials. Furthermore, as softer materials, such synthetic fibers tend to be less of an irritant to the skin, and therefore are less likely to cause rashes or other adverse skin reactions typically associated with the harder or abrasive cleansers. Such synthetic fibers are also abundant in supply and easily produced. Strands of these fibers are available in many diameters, and easily cut to desired lengths for incorporation into the shaving composition. The optimal synthetic fiber diameter should be on the order of the typical blade edge thickness, or roughly about 50 to about 200 μm; however, other diameters may also be utilized. In order to allow the maximum coverage area for micro-blade support, the aspect ratio of the chosen polymeric fiber additives are preferably from about 3:1 to about 5:1, that is the fiber length is preferably about 3 to 5 times greater than the diameter of the fiber; however, aspect ratios below 3:1 and above 5:1 can also be employed if preferred. As noted above, an effective amount of insoluble particulate additives is an amount, by weight, which provides physical support for the blade of a razor blade assembly during the shaving process. In most instances, from about 0.1% to about 20%, by weight will be adequate, while from about 1% to about 10%, by weight is preferred. However, it is to be understood that in some instance an equivalent "effective amount" of insoluble particulate additives less than 0.1% and greater than 20%, and in thick pastes and gels even as high as 90% or greater may be used in the practice of the present invention.

The shaving media of the present invention is easily adapted for employment with standard or conventional pressurized or aerosol dispensers commonly available for commercial shaving creams and gels, or solid-stick applicators. Such application methods are described in U.S. Pat. Nos. 5,174,992 by Lindauer, et. al., or 4,145,411 by Mende. Since the shaving compositions of the present invention may incorporate a single solid additive or combination of solid additives, no special considerations for media delivery must be reconciled. The minute size of the particles incorporated into the shaving composition allows easy passage from the stable in-situ composition container to the air via traditional dispensing nozzles which incorporate large openings and travel diameters, typically on the order of 10 millimeters or more. Standard aerosol propellants may be employed in the delivery of the shaving compositions of the present invention.

As noted above, the present invention encompasses any and all shaving compositions, whether in solid, gel, cream, liquid or aerosol form, incorporating insoluble particulate additives which provide improved blade glide, improved hair retraction from skin, and reduced skin abrasion, cutting and nicking over irregular surfaces or skin abnormalities.

It is therefore seen that the shaving compositions of the present invention are clearly different not only from prior art shaving compositions, but also clearly different from abrasive facial scrubs, cleaning compounds, and general soaps. Furthermore, the present invention is clearly discernable from prior art shaving compositions which employ soluble materials in shaving compositions for improved lubricity. In addition, it is seen that the compositions of the present invention which provide shaving compositions in which insoluble particulate additives, such as organic or inorganic fillers or abrasive materials, are incorporated. It has been shown that when such shaving compositions are used with conventional razor blade assemblies they will minimize nicks and cuts, and yet will provide a close shave, and improve post-shave skin smoothness, and improved cleansing characteristics.

The foregoing exemplary descriptions and the preferred embodiments of the present invention have been explained in detail, with varying modifications and alternative embodiments being taught. While the invention has been so shown and described, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. Shaving compositions for use in the personal shaving process with a razor blade assembly, which shaving compositions provide physical, microscopic support for the blade of such a razor blade assembly during the personal shaving process including:

a mixture of at least one wetting agent, at least one cleansing agent, at least one lather producing composition, and at least one emollient; and further including at least one solid, insoluble particulate additive in a well dispersed suspension throughout said shaving composition, said solid additives present in an effective amount to produce physical support for the blade of a razor blade assembly during the personal shaving process.

2. The compositions according to claim 1 wherein said solid, insoluble particulate additives are selected from the group consisting of organic polymers particles and inorganic particles.

3. The compositions according to claim 2 wherein said solid, insoluble particulate additives are in a size range of from about 0.1 μm to about 1,000 μm.

4. The compositions according to claim 2 wherein said solid, insoluble particulate additives are in a size range of from about 10 μm to about 500 μm.

5. The compositions according to claim 2 wherein said solid, insoluble particulate additives are in a size range of from about 50 μm to about 200 μm.

6. The compositions according to claim 2 wherein said effective amount of said solid, insoluble particulate additives is from about 0.1% to about 20% by weight.

7. The compositions according to claim 2 wherein said effective amount of said solid, insoluble particulate additives is from about 1% to about 10% by weight.

8. The compositions according to claim 2 wherein said solid, insoluble particulate additives are selected from the group consisting of acetal resins, aluminum oxide, boron carbide, calcium carbonate, calcium phosphate, calcium silicate, diatomaceous earth, polyamides, polyethylenes, polytetrafluoroethylene, polypropylene, polyurethane, silica, pumice, quartz, silicon nitride, silicon carbide, titanium dioxide, and wood, and mixtures thereof.

9. The compositions according to claim 2 wherein said solid, insoluble particulate additives include inorganic particles selected from the group consisting of aluminum oxide, boron carbide, calcium carbonate, calcium phosphate, calcium silicate, diatomaceous earth, silica, pumice, quartz, silicon nitride, silicon carbide, titanium dioxide, and wood, and mixtures thereof.

10. The compositions according to claim 9 wherein said solid, insoluble particulate additives include silica in the size range of from about 50 μm to about 200 μm.

11. The compositions according to claim 2 wherein said solid, insoluble particulate additives include organic polymer particles selected from the group consisting of acetal resins, polyamides, polyethylenes, polytetrafluoroethylene, polypropylene, and polyurethane, and mixtures thereof.

12. The compositions according to claim 11 wherein said solid, insoluble particulate additives include organic polymer particles are in the form of polymeric fibers having a length and diameter dimension.

13. The compositions according to claim 12 wherein said solid, insoluble particulate additive fibers have a length in the range of between about three to about five times the fiber diameter.

14. The compositions according to claim 13 wherein said solid, insoluble particulate additive fibers have a diameter of between about 10 μm and about 500 μm.

15. The compositions according to claim 14 wherein each of said fibers include polyamide.

16. The compositions according to claim 2 wherein said solid, insoluble particulate additives are in a size range of from about 50 μm to about 200 μm, and wherein said effective amount of said solid, insoluble particulate additives is from about 0.1% to about 20% by weight.

17. Shaving compositions for use in the personal shaving process with a razor blade assembly, which shaving compositions provide physical support for the blade of such a razor blade assembly during the shaving process including:

a mixture of at least one wetting agent, at least one cleansing agent, at least one lather producing composition, and at least one emollient; and further including solid, insoluble particulate silica additive in a well dispersed suspension throughout said shaving composition; whereby said the solid silica additive produces a physical support for the blade of a razor blade assembly during the shaving process.

18. The compositions according to claim 17 wherein said solid, insoluble silica particulate additive is in a size range of from about 50 μm to about 200 82 m, and wherein said effective amount of said solid, insoluble particulate additives is from about 0.1% to about 20% by weight.

19. Shaving compositions for use in the personal shaving process with a razor blade assembly, which shaving compositions provide physical microscopic support for the blade of such a razor blade assembly during the personal shaving process, including:

a mixture of at least one wetting agent, at least one cleansing agent, at least one lather producing composition, and at least one emollient; and further including solid, insoluble particulate polyamide fiber additive in a well dispersed suspension throughout said shaving composition; whereby said the solid polyamide fiber additive produces a physical support for the blade of a razor blade assembly during the shaving process.

20. The compositions according to claim 19 wherein said solid, insoluble particulate polyamide fiber additives have a length in the range of between about three to about five times the fiber diameter.

21. The compositions according to claim 20 wherein said solid, insoluble particulate polyamide fiber additives have a diameter of between about 10 μm and about 500 μm, and wherein said effective amount of said solid, insoluble particulate additives is from about 0.1% to about 20% by weight.

* * * * *

UNITED STATES PATENT AND TRADEMARK OFFICE
CERTIFICATE OF CORRECTION

Patent No.  : 5,587,156
Dated       : Dec. 24, 1996
Inventor    : Mark S. Wdowik It is certified that errors appear in the above-identified patent and that said Letters Patent is hereby corrected as shown below:

In the Claims:

Claim 18, line 3, please delete "200 82 m" and replace it with --200 $\mu$m--.

Signed and Sealed this

Twenty-first Day of November, 2000

Attest:

Q. TODD DICKINSON

Attesting Officer  Director of Patents and Trademarks